United States Patent [19]

Kaltenbach et al.

[11] 4,180,812
[45] Dec. 25, 1979

[54] DENTAL TREATMENT APPARATUS

[75] Inventors: Kurt Kaltenbach, Biberach; Martin Saupe, Mittelbiberach; Stefan Beier, Biberach; Hermann Gmeinder, Biberach; Hartmut Braetsch, Biberach, all of Fed. Rep. of Germany

[73] Assignee: Kaltenbach & Voight GmbH & Co., Biberach an der Riss, Fed. Rep. of Germany

[21] Appl. No.: 892,274

[22] Filed: Mar. 31, 1978

[30] Foreign Application Priority Data

Apr. 7, 1977 [DE] Fed. Rep. of Germany ....... 2715798

[51] Int. Cl.² ............................................. G06K 15/18
[52] U.S. Cl. ................................. 340/706; 340/147 P; 340/798; 433/28; 364/200; 433/101
[58] Field of Search ............ 32/22, DIG. 3; 340/706, 340/798, 152 R, 147 P; 364/200, 900

[56] References Cited

U.S. PATENT DOCUMENTS

| | | | |
|---|---|---|---|
| 3,719,926 | 3/1973 | Sangster et al. | 340/147 P |
| 3,989,952 | 11/1976 | Hohmann | 32/22 X |
| 4,094,069 | 6/1978 | Cope | 32/22 |

Primary Examiner—David L. Trafton
Attorney, Agent, or Firm—Scully, Scott, Murphy & Presser

[57] ABSTRACT

A dental treatment apparatus having a plurality of dental instruments releasably retained in an instrument-holding device. A control and display arrangement controls the operation of an instrument upon extraction from the holding device, and displays the magnitude of an operating parameter of the instrument on a display device. A control data store is arranged to store predetermined fixed control data values for the operating parameters of the instruments. To enable the user to alter the predetermined fixed values, a forward-backward counter is connected to the data store which can also store the altered values. A data converter is connected to the counter and to the display device for converting the instantaneous value stored in the data store to a corresponding service datum instantaneous value to be displayed by the display device.

13 Claims, 3 Drawing Figures

Fig.3
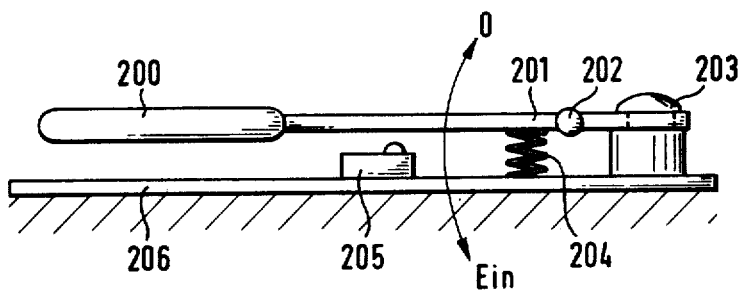
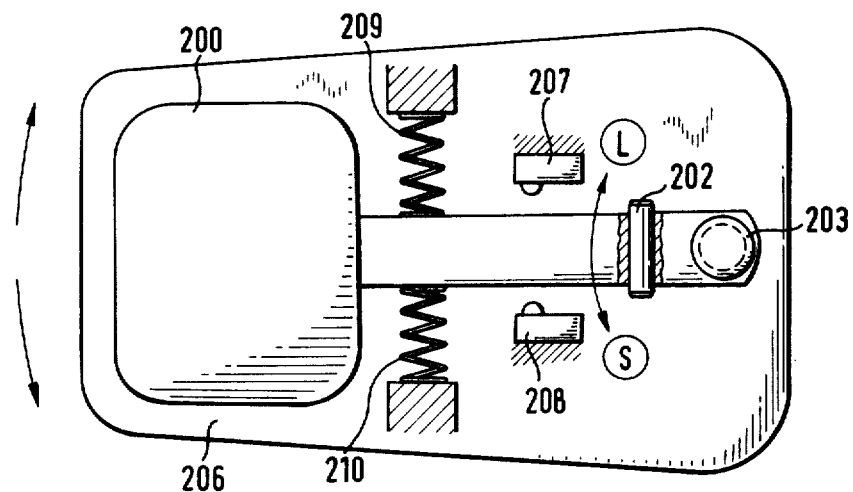

DENTAL TREATMENT APPARATUS

This invention relates to a dental treatment apparatus having at least one dental treatment instrument—for example a drilling machine, a control data store for storing pre-determined control fixed values, for example determined speeds of a drilling machine, which are stored and are adapted to be selectively called, and a display device for displaying the magnitude of an operating parameter of the instrument.

A known dental treatment apparatus (German Offenlegungsschrift No. 1,491,094) has a plurality of electronic or electro-mechanical control construction groups individually operated by a foot-key switching set. Each control construction group is desinged for a pre-determined speed of a dental drilling machine. The speeds of the drilling machine are in this case to be considered to be control data. The control construction groups (or control assemblies, control structural components) may be considered to be control data stores. The control assemblies are electrically connected with an optical display device of known construction, indicating the switching condition.

The known dental treatment apparatus has a number of disadvantages. One disadvantage consists that the dentist is limited to the preselected speeds. Variation of speed between the pre-selectable fixed values is impossible, which is, however, desirable for sensitive treatment.

A further disadvantage is that, with selection of the corresponding control assembly, in the display device there merely lights-up a lamp associated therewith. If there is set up on the drilling machine an attachment instrument having a predetermined transmission ratio, then it is necessary for the dentist to first of all mentally to convert in order to establish the service speed which the drilling implement actually has. Generally speaking this means that it is not recognisable at the display device if the service data deviate from the control data.

It is an object of the invention to provide a treatment apparatus which obviates the above-mentioned disadvantages.

According to one aspect the invention provides a dental treatment apparatus having a dental instrument, and a control and display arrangement for controlling the operation of the dental instrument and for displaying the magnitude of an operating parameter of the dental instrument, said control and display arrangement comprising:

a control data store for storing a pre-determined fixed control datum value for said operating parameter of the dental instrument;

a display device operable to display the magnitude of said operating parameter of the dental instrument;

control means connected to said control data store and operable to vary the pre-determined fixed control datum value to a further instantaneous value as desired, said instantaneous value being stored in the data store as a further fixed value;

and a data converter connected to said control means and to said display device for converting the instantaneous value stored in the data store to a corresponding service datum instantaneous value to be displayed by said display device.

Thus, using the treatment apparatus according to the invention, the dentist is in a position to store service data of his own selection as fixed values. With these fixed values, the treatment instrument commences on putting into operation taking-place. The dentist is, however, able to deviate from the fixed values and to vary the service data. Both the fixed values and also the varied service data can be read-off the display device by the dentist. Subsequent to termination of treatment, the treatment instrument once again commences, subsequent to renewed putting into operation, at the stored fixed value, doing so in fact also when the service data at the end of the previous treatment have deviated from the fixed values. The data converter ensures in each particular instance that there are displayed on the display device not the control data but the service data. As stated, the control data may deviate from the service data if for example there is provided a drilling machine incorporating or provided with a transmission (step-up or step-down).

In a preferred arrangement the conversion ratio may be selectively adjustable. Thereby, it becomes possible, in addition to application instruments having varying transmission ratios, to employ for a drilling machine also still further treatment instruments having varying operation zones and/or dimensions of the service data. In addition to a drilling machine, for example, it is possible to employ also a tartar remover the service data of which characterise the oscillation amplitude. A further example is the employment of a UV-hardener for tooth fillings. In this case, the operating or service data are characterised by the hardness time. Due to a conversion ratio which in each particular instance is different in the data converter, it is possible in each particular instance to display the correct service data on the display device.

A practical embodiment of the invention may comprise control means having a forward-backward counter coupled with a starter by means of which the counter is adapted to be set in forward operation and in backward operation, the counter being connected to the control data store and to the data converter.

A further development may consist in that the counter has a pulse input connected with a cadencing pulse transmitter, in that the counter has a set input connected via a branch of a data switch-point with the control data store, in that the output of the counter is connected with the data converter and via the other branch of the data switch-point with the control data store, and in that the data switch-point and the counter are adapted to be activated by a set command triggered on putting the instrument into operation for setting the counter.

If the treatment apparatus is equipped with a plurality of treatment instruments adapted to be deposited in an instrument holding device, each instrument actuating a switch associated with it on extraction taking place, then another preferred development may consist in that the switches of the holding device are connected to an instrument coder for generating an address signal characteristic of the extracted instrument, in that the control data store has at least a number of registers equal with the number of treatment instruments, each register being associated with a treatment instrument, and in that the address signal is fed to the control data store so as to activate the register associated with the extracted instrument for connection to the data switch-point.

The control data store and the data switch-point may be activated for example by means of a setting key for re-storing control data in the control data store.

The data switch-point and the control data store may be connected by a setting command line to the instrument coder and, on extraction of an instrument from the holding device, be subjected to the action of a setting command.

A practical carrying into effect of the data converter may consist in that it comprises a plurality of parallel-connected fixed ratio converters having varying conversion ratios and also a fixed ratio selector with which the individual fixed ratio converters are activatable.

According to a preferred embodiment of the invention, a numerical display device is employed.

A further practical further development of the invention may consist in that there is associated with the fixed ratio selector an allocation store having at least a number of storage cells equal with the number of instruments, in that there is associated with the fixed ratio selector furthermore a number of selection keys equal to the number of fixed ratio converters, and which are connected with a fixed ratio coder which, on keying generates a fixed ratio signal characteristic for the selected fixed ratio, the address signal and the fixed ratio signal being fed to the allocation store as to write the fixed ratio signal into the register corresponding to the instrument extracted from the holding device, and in that there is associated with the fixed ratio selector a fixed ratio decoder connected to the allocation store and which decodes the fixed ratio signal and activates the corresponding fixed ratio converter.

The control data supplied from the control element may also be fed to a computer, preferably a microprocessor to which are fed furthermore supplementary data, for instance such as relating to the material nature of the material to be processed or treated, to the material layer thickness to be removed, to the diameter, the hardness and the cut properties of the instrument, etc., the computer computing therefrom optimated (programmed) control data according to a read-in programme, and supplying them to the instrument concerned. Independent inventive significance is attributed to this idea.

Accordingly, in another aspect the invention comprises a dental treatment apparatus having a plurality of dental instruments, a holding device for releasably holding said instruments, and a control and display arrangement for controlling the operation of the instruments and for displaying the magnitude of operating parameters of the instruments, said control and display arrangement comprising:

control means for controlling the operation of each instrument upon removal from said holding device;

a computer arranged to be supplied with data relating to operating factors for the instruments such as the cutting velocity, the initial velocity, the operating zone, instrument diameter, the nature and character of the material to be processed, and instrument hardness and cutting properties, said computer being arranged to calculate from such data optimum control data and service data, the control data being supplied to said control means;

and a display device arranged to be supplied with said service data from said computer.

Another expedient further development relates to the starter which must be specially designed for operation of the forward-backward counter. In this further development the starter comprises a lever mounted for pivotal movement about a substantially horizontal axis and about a substantially vertical axis, a foot pedal secured to one end of said lever, first spring means arranged resiliently to resist downward movement of said foot pedal about said horizontal axis, second spring means arranged resiliently to resist movement in either direction of said foot pedal about said vertical axis, a switch responsive to said downward movement of the foot pedal in order to control the operation of a dental instrument, and further switches arranged one on each side of said lever to respond to movement of the foot pedal about said vertical axis in order to control the operation of said counter, one of said further switches setting the counter in forward-counting operation and the other of said further switches setting the counter in backward-counting operation.

BRIEF DESCRIPTION OF THE DRAWINGS

FIG. 3 shows a foot operated key in side elevation and in plan view, for controlling the operation of the dental treatment apparatus.

DESCRIPTION OF PREFERRED EMBODIMENTS

Figure 1:
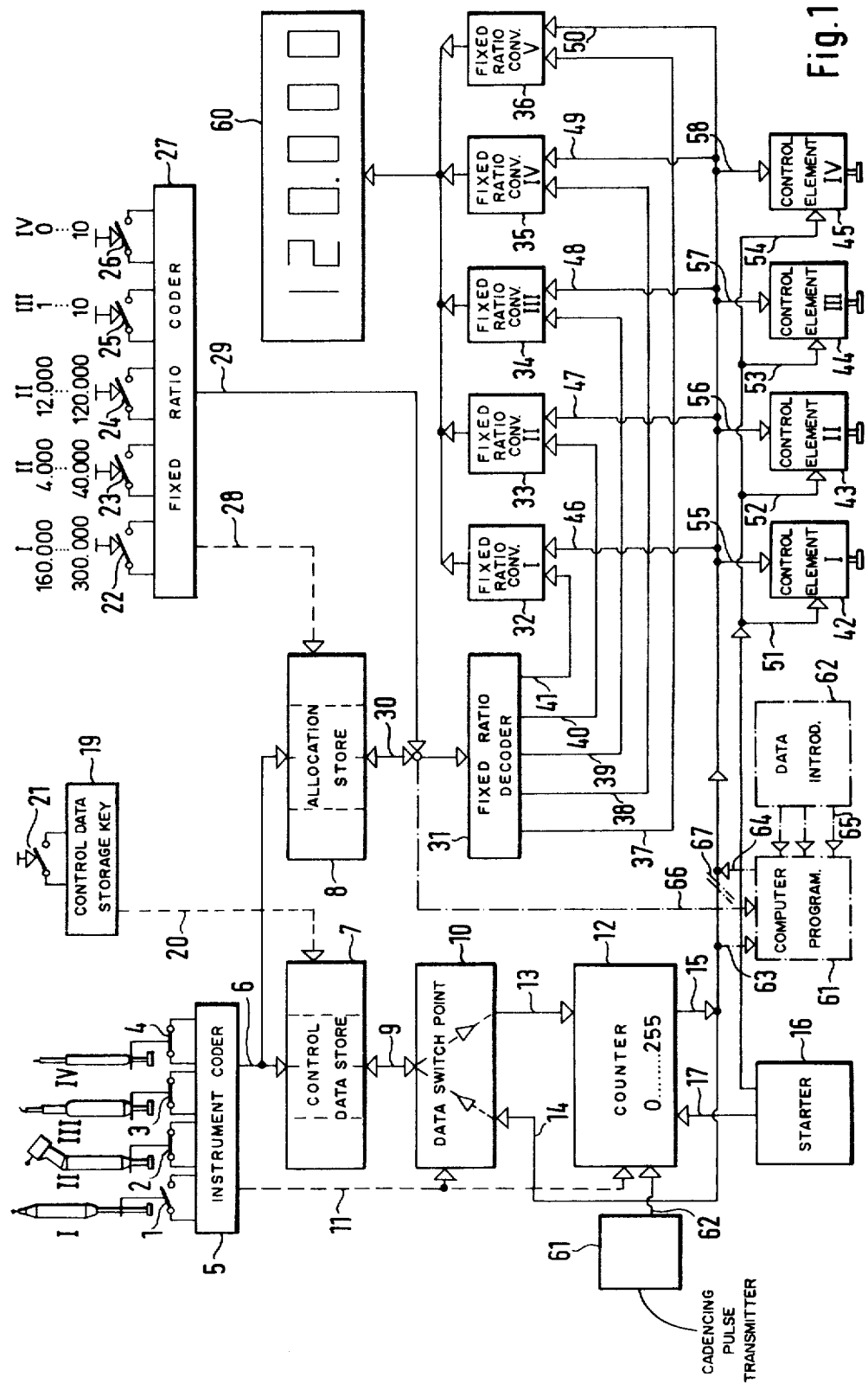
FIG. 1 is a circuit diagram of a first embodiment of dental treatment apparatus according to the invention.

A dental treatment station shown in FIG. 1 has four treatment instruments I-IV. The treatment instrument I is a turbine drill, the instrument II is an electrically driven drill, the instrument III is a tartar remover, and the instrument IV is a UV-hardener.

The four instruments I-IV are arranged in an instrument-holding device. The instruments II-IV are arranged to close associated switches 2, 3 and 4, and the instrument I is drawn-out in order to open the switch 1 associated therewith.

The four switches 1 to 4 are coupled with an instrument coder 5 which is arranged to generate an address signal at its output 6. The address signal, in the case of four instruments, is a two bit signal.

Control of the instruments is effected by a forward-backward counter 12 connected via a data line 62 with a (cadencing) pulse transmitter 61 and capable of counting from zero to 255. By means of a starter 16, the counter 12 can be set via a data line 17 in a forward-counting operation or a backward-counting operation. The state of the counter 12 is fed via an output line 15 and input lines 55 to 58 to final control elements 42 to 45 for the four instruments I-IV. A high counter state signifies a high speed for the turbine I and the drill II, whereas a high counter state for the tartar remover III signifies a high oscillation amplitude and for the UV-hardener IV it signifies a long hardening time.

The output of the counter 12 is also fed via a data line 14 to a data switch-point 10. The latter is coupled via a data line 9 with a control data store 7. The control data store 7 has four registers, each register being associated with a respective one of the instruments. Via the address line 6, there is fed to the control data store 7 an address by means of which that register is activated which corresponds to the particular instrument withdrawn from the holding device.

The control data store 7 is furthermore connected via the data line 9, the data switch-point 10 and a data line 13 with a set input of the counter 12.

Stored in the control data store 7 are fixed values of the control data pre-determined for each instrument. If, as in the present case, the instrument I is withdrawn, then the first register of the control data store 7 is activated via the address line 6. Simultaneously, the data switch-point 10 and the counter 12 receive a setting pulse from the instrument coder 5 via a setting pulse line 11. Due to this setting pulse, the data switch-point 10 is switched temporarily to passage from the control data store 7 to the counter 12. Thereby, the counter 12 is set at the fixed value stored in the control data store 7 e.g. in the first register when it is the instrument I which is withdrawn. This may for example be the counter state 181. After decay of the setting pulse, the data switch-point 10 once again switches over into its normal condition. In this condition, it is set at passage from the counter 12 to the control data store 7.

On actuation of the starter 16, the final control element 42 for the instrument I is subjected to the action of the counter value of the counter 12. This was, in the present case, 181. When the dentist ascertains that the speed corresponding to the counter value 181 is rather too high, by means of the starter 16 he can put the counter 12 into backward-counting operation. The counter 12 then counts for example up to 155. If the dentist now ascertains that the speed corresponding to this counter value is more advantageous, then he is able to store it in the control data store 7. For this purpose, he must actuate a store key 21 which induces a pulse generator 19 to transmit, via a data line 20, a setting pulse to the control data store 7. Since the control data store 7 is connected with the output of the counter 12, via the line 9, the data switch-point 10 and the lines 14 and 15, the adjusted counter state is now stored in the first register of the control data store 7. Similarly adjusted data can be stored in the registers in the data store 7 corresponding to instruments II–IV.

For the instruments I to IV, various operating zones or ranges having corresponding, varying service data are provided. The operating zones can be set at keys which, on actuation, close switches 22 to 26. For the instrument I (turbine), there may be operating speeds of 160,000 to 300,000 revolutions per minute. For the instrument II (electro-drill) there is provided a first operating range between 4,000 and 40,000 revolutions per minute. Due to an attachment having a transmission ratio 1:3, the service speed of the electro-drill can be increased to between 12,000 and 120,000 revolutions per minute. For the tartar remover, oscillation amplitudes having the standard values of 1 to 10 are provided as operational range. For the UV-hardener, the operational range is between 0 and 10 sec.

The actual service data are indicated at a numerical display device 60 having 6 positions. Referring to FIG. 1, the display device 60 indicates, for example, 120,000 revolutions per minute for the instrument I.

The service data are in a proportional ratio to the control data or to the counter value of the counter 12. For display, the counter value or the control data must, however, be converted. Conversion is effected in accordance with a pre-determined fixed ratio which differs for each operating zone or range. For the five different operating ranges, therefore, there are provided five fixed ratio converters 32 to 36. The counter state of the counter 12 is fed to the fixed ratio converters 32 to 36 via the lines 15 and 46 to 50. Via the line 59, the fixed ratio converter activated in each particular instance then supplies the converted value to the display device 60.

In order that the dentist may be able to exchange the instruments in the holding device, for example because a pre-determined arrangement is most convenient for him in accordance with custom, an association must be established between the individual fixed ratio converters 32 to 36 and the deposition points of the instruments I to IV. For this purpose, the switches 22 to 26 of the fixed ratio keying selector are connected with a fixed ratio coder 27. The latter generates for the five operating ranges a signal having three bits and which is suitable for identification of the keyed operating range.

A signal line 29 is connected via a further signal line 30 with an allocation store 8 provided with four registers. Each register is associated with a respective instrument. The allocation store 8 is also connected to the address line 6 coming from the instrument coder 5. Upon receiving a particular address signal, the corresponding register in the allocation store 8 can be activated.

If, for example, the instrument II is withdrawn, then the second register in the allocation store 8 is activated. Then, either the service range 4,000 to 40,000 revolutions per minute or the service range 12,000 to 120,000 revolutions per minute can be fed into this register. For this keying or read-in, by pressing the corresponding key, from the fixed ratio coder 27 via the data line 28 a set pulse can be transmitted to the allocation store 8. By withdrawing any other of the instruments and by pressing the corresponding key of the fixed ratio selector, also the other registers of the allocation store 8 can be set. If the positions of the instruments in the depositing location are to be exchanged, then the allocation store 8 must be re-set.

The fixed ratio stored or the service range of the register of the allocation store 8 activated by the address signal is fed via the data line 30 to a fixed ratio decoder 31. The latter decodes the stored 3-bit word and activates that one of the fixed ratio converters 32 to 36 via the associated data line 37 to 41 which corresponds to the fixed ratio or operating range called by the allocation store 8. If for example the turbine I is withdrawn, then the fixed ratio converter 31 is activated. Thereby, the counter value of the forward-backward counter 12 is so converted that it supplies, in the display device 60, e.g. the speed value of 120,000 revolutions per minute.

In order to make it possible to a high degree for the dentist to effect his work economically and in medically optimum fashion, there may be connected in the circuit also a circuit element as shown in dot-dash line. What is concerned is a computer 61 into which pre-determined parameters may be fed via a data introduction arrangement 62. These parameters are, for example, the diameter and the nature of the drill (for example rose drill or spiral drill) or the hardness of the implement (for example hard metal or diamond). Furthermore, there may be fed-in data relating to the thickness and hardness of the material layer to be removed. Via a data line 66 shown in dot-dash line, the computer furthermore receives the information with regard to the selected operating range. The counter state of the counter 12 is fed to the computer via a line 63. The computer 61 then calculates in accordance with a programme contained in it, an optimum value which is between zero and 250 but may deviate from the state of the counter 12. This value is fed to the line (interrupted at point 67) which normally feeds the starting value of the counter 12 to the fixed ratio converter, or passes on the final control element, via a line 64.

Such optimum values can, on feeding-in the corresponding parameters, be calculated of course for all instruments.

Since the forward-backward counter has only 256 counter values whereas the display device 60 is able to display up to the number 999,999 it is necessary to "jump over" pre-determined numerical zones of the display device. However, this has no disadvantageous influence on the dentist's work, since display accuracy of 1/255, i.e. of 4 Promille, is completely adequate.

Figure 2:
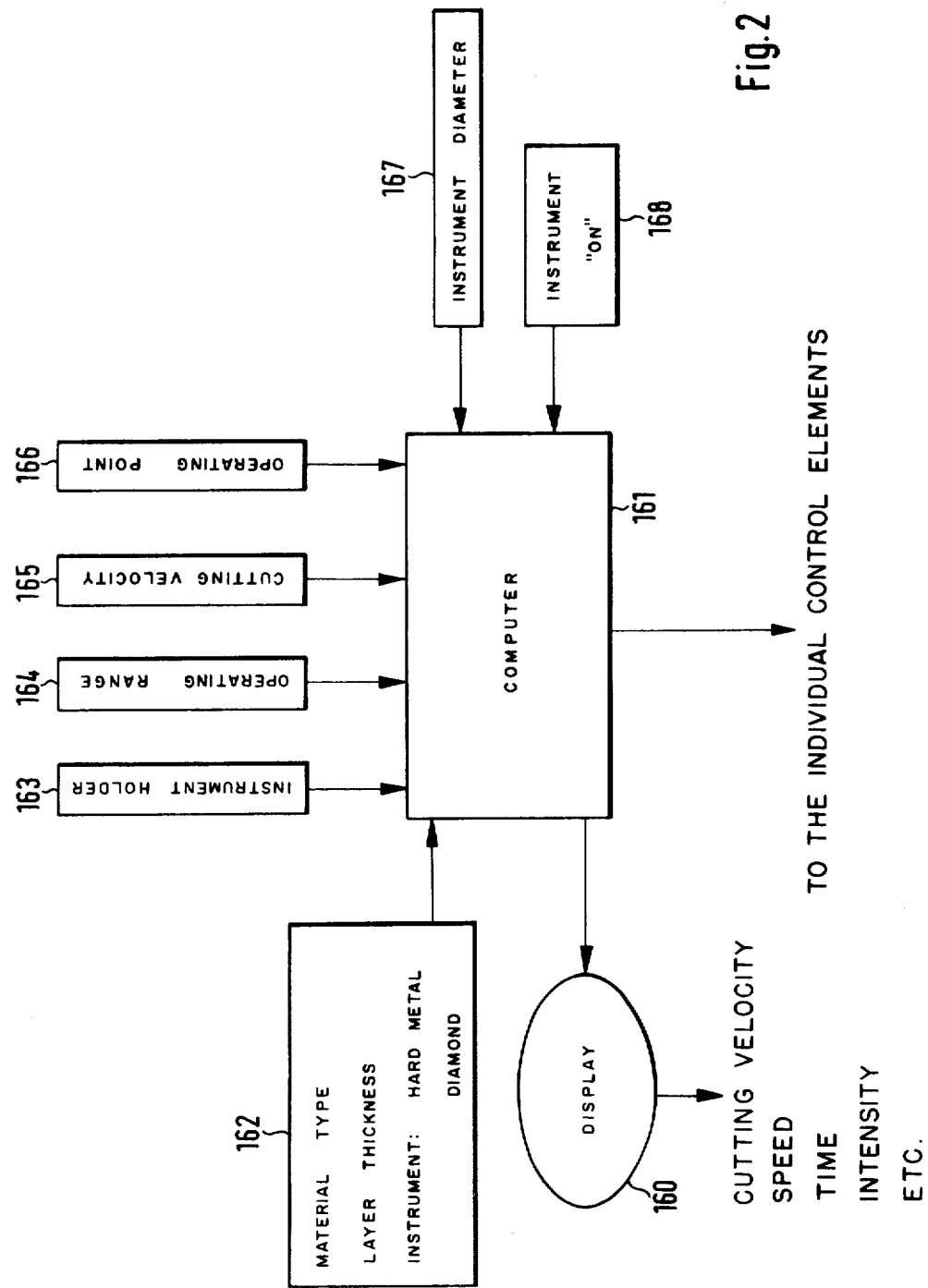
FIG. 2 is a generalised block circuit diagram of a second embodiment of the invention.

FIG. 2 shows a generalised block circuit diagram demonstrating the possibility, with the aid of a computer 161 and subsequent to feed-in of the desired service data and parameters, of circulating and generating programmed control information for the final control elements and display information for the display device. There are fed into the computer 161, according to block 162, for example information with regard to the material nature, the layer thickness and also the tool hardness. According to block 163, the computer 161 is coupled with the instrument holding device and the switches. The desired data of the operating range are adapted to be fed into the computer 161 according to the block 164. The cut velocity is fed-in via the block 165. The operating point, i.e. the operating data for initiation are fed-in via block 166. Via block 167, the instrument diameter is fed-in. 168 characterises the starter with which cutting-in and out of the instruments is possible, and also increase or reduction of the operating data. Display of the data computed by the computer 161 is effected via a display device 160. The latter displays, depending on the selected instruments, the cut velocity, the speed, the time, the intensity, etc.

FIG. 3 shows a foot-operated starter for actuating the forward-backward counter 12 shown in FIG. 1. It comprises a footrest 200 secured at the end of a lever 201. The lever 201 is pivotal by means of a first joint 202 about a horizontal pivot and by means of a second joint 203 about a vertical pivot. The first joint 202 is secured on a base plate 206. By loading the footrest 201 from above, the latter can be pressed downwardly against the action of a spring 204 bearing on the base plate 206, the lever 201 thereby actuating a microswitch 205. This serves for the cutting-in and out of the selected instrument. Due to lateral deflection of the footrest 200 against the action of springs 209, 210, bearing at elements connected to the base plate 206, microswitches 207, 208 arranged laterally adjacent the lever 201 can be actuated. With the aid of the microswitches 207, 208, the counter 12 can be set in forward-counting operation or in backward counting operations.

We claim:

1. A dental treatment apparatus having a dental instrument, and a control and display arrangement for controlling the operation of the dental instrument and for displaying the magnitude of an operating parameter of the dental instrument, said control and display arrangement comprising:

a control data store for storing a pre-determined fixed control datum value for said operating parameter of the dental instrument;

a display device operable to display the magnitude of said operating parameter of the dental instrument;

control means connected to said control data store and operable to vary the pre-determined fixed control datum value to a further instantaneous value as desired, said instantaneous value being stored in the data store as a further value;

and a data converter connected to said control means and to said display device for converting the instantaneous value stored in the data store to a corresponding service datum instantaneous value to be displayed by said display device.

2. A dental treatment apparatus according to claim 1, in which the conversion ratio is selectively adjustable.

3. A dental treatment apparatus according to claim 1, in which the control means comprises a forward-backward counter, a starter coupled with said counter for setting the counter in forward-counting operation and backward-counting operation relative to said predetermined value, said counter being connected to said control data store and to said data converter.

4. A dental treatment apparatus according to claim 3, in which said counter has a pulse input connected to a cadencing pulse transmitter, said counter has a setting input connected via a branch of a data switch-point to said control data store, an output of said counter is connected to said data converter and via another branch of said data switch-point to said control data store, and said data switch-point and said counter are adapted to be activated by a set command for setting said counter following the putting into operation of said instrument.

5. A dental treatment apparatus according to claim 4, having a plurality of dental instruments adapted to be deposited in an instrument-holding device, each instrument being arranged to actuate a respective switch associated therewith upon extraction of the instrument from the holding device, an instrument coder connected to said switches for generating an address signal characteristic of each instrument upon extraction from said holding device, and a number of registers provided in said control data store corresponding to the number of instruments, each register being associated with a respective instrument, and being actuated in response to the supply to the control data store of an address signal corresponding to extraction of the instrument from the holding device for connection to said data switch-point.

6. A dental treatment apparatus according to claim 4, including a set-key operable to actuate said control data store and said data switch-point for the re-storing of data in said control data store.

7. A dental treatment apparatus according to claim 5, including a setting command line connecting said data switch-point and said control data store to said instrument coder and operable, upon extraction of any one of the instruments from said holding device, to supply a setting command signal.

8. A dental treatment apparatus according to claim 4, in which said data converter comprises a plurality of parallel-connected fixed ratio converters having varying conversion ratios and also a fixed ratio selector with which the individual fixed ratio converters are activatable.

9. A dental treatment apparatus according to claim 8, in which said display device is a numerical display device.

10. A dental treatment apparatus according to claim 8, including an allocation store associated with said fixed ratio selector and having a number of storage cells equal to the number of instruments, said fixed ratio selector furthermore having a number of selector keys equal to the number of fixed ratio converters and which are connected with a fixed ratio coder which, on keying taking place, generates a fixed ratio signal characteristic of the selected fixed ratio, there being fed to said allocation store the address signal and the fixed ratio signal in order to write the fixed ratio signal into the register corresponding to the instrument extracted from the holding device, and in which there is associated with said fixed ratio selector a fixed ratio decoder connected to said allocation store for decoding the fixed ratio signal and for activating the corresponding fixed ratio converter.

11. A dental treatment apparatus according to claim 1, including a computer, preferably a micro-processor, arranged to be supplied by said control means, there being fed to said computer further supplementary data selected from the material nature of the material to be processed or treated, the material layer thickness to be removed, the diameter, and the hardness and the cutting properties of the instrument, and said computer being arranged to compute therefrom programmed control data in accordance with a read-in programme.

12. A dental treatment apparatus having a plurality of dental instruments, a holding device for releasably holding said instruments, and a control and display arrangement for controlling the operation of the instruments and for displaying the magnitude of operating parameters of the instruments, said control and display arrangement comprising:

control means for controlling the operation of each instrument upon removal from said holding device;

a computer arranged to be supplied with data relating to operating factors for the instruments such as the cutting velocity, the initial velocity, the operating zone, instrument diameter, the nature and character of the material to be processed, and instrument hardness and cutting properties, said computer being arranged to calculate from such data optimum control data and service data, the control data being supplied to said control means;

and a display device arranged to be supplied with said service data from said computer.

13. A dental treatment apparatus according to claim 3, in which said starter comprises a lever mounted for pivotal movement about a substantially horizontal axis and about a substantially vertical axis, a foot pedal secured to one end of said lever, first spring means arranged resiliently to resist downward movement of said foot pedal about said horizontal axis, second spring means arranged resiliently to resist movement in either direction of said foot pedal about said vertical axis, a switch responsive to said downward movement of the foot pedal in order to control the operation of a dental instrument, and further switches arranged one on each side of said lever to respond to movement of the foot pedal about said vertical axis in order to control the operation of said counter, one of said further switches setting the counter in forward-counting operation and the other of said further switches setting the counter in backward-counting operation.

* * * * *